United States Patent [19]

Mueller, Jr.

[11] Patent Number: 4,938,220
[45] Date of Patent: Jul. 3, 1990

[54] CATHETER WITH SPLIT TIP MARKER AND METHOD OF MANUFACTURE

[75] Inventor: Richard L. Mueller, Jr., Mountain View, Calif.

[73] Assignee: Advanced Cardiovascular Systems, Inc., Santa Clara, Calif.

[21] Appl. No.: 298,865

[22] Filed: Jan. 13, 1989

Related U.S. Application Data

[63] Continuation of Ser. No. 891,790, Aug. 1, 1986, abandoned.

[51] Int. Cl.⁵ ............................................. A61M 25/10
[52] U.S. Cl. ................................. 128/658; 604/96; 606/194
[58] Field of Search .................. 128/653–654, 128/656–658, 341, 344, 772; 604/20, 96–104, 280

[56] References Cited

U.S. PATENT DOCUMENTS

| | | | |
|---|---|---|---|
| 4,041,931 | 8/1977 | Elliott et al. | 128/1 R |
| 4,419,095 | 12/1983 | Nebergau et al. | 604/96 |
| 4,571,240 | 2/1986 | Samson et al. | 128/658 X |
| 4,597,755 | 7/1986 | Samson et al. | 604/280 X |
| 4,665,925 | 5/1987 | Millar | 604/96 X |
| 4,684,363 | 8/1987 | Ari et al. | 604/104 X |
| 4,693,237 | 9/1987 | Hoffman et al. | 128/1 R |
| 4,715,378 | 12/1987 | Pope, Jr. et al. | 604/96 X |

FOREIGN PATENT DOCUMENTS

| | | | |
|---|---|---|---|
| 0033659 | 8/1981 | European Pat. Off. | 128/658 |
| 0940777 | 7/1982 | U.S.S.R. | 128/658 |
| 1435797 | 5/1976 | United Kingdom | 128/657 |

Primary Examiner—Angela D. Sykes
Attorney, Agent, or Firm—Fulwider, Patton, Lee & Urecht

[57] ABSTRACT

Dilatation cathether, tip marker and method of manufacture wherein the tip marker comprises a split sleeve of radiopaque material having an arc length between 180° and 360°. In one disclosed embodiment, the tip marker is crimped in position about an inner tubular member, and an outer tubular member is bonded to the inner tubular member, with the tip marker being captured between the two members. In this particular embodiment, the outer tubular member comprises an inflatable balloon, and a vent opening extends from the balloon to the distal end of the catheter through the gap formed between the confronting edges of the marker sleeve.

7 Claims, 1 Drawing Sheet

CATHETER WITH SPLIT TIP MARKER AND METHOD OF MANUFACTURE

This application is a continuation, of application Ser. No. 891,790, filed Aug. 1, 1986, now abandoned.

BACKGROUND OF THE INVENTION

This invention pertains generally to medical appliances, and more particularly to an angioplasty catheter having a fluoroscopically visible tip marker and to a method of manufacturing the same.

Fluoroscopically visible tip markers permit the positions of dilatation catheters and the like to be monitored as they are inserted into the vascular system of a patient. Such markers typically consist of one or more bands of radiopaque material mounted on the distal end portion of the catheter. Unfortunately, these bands cannot also be installed without interfering with other functions of the catheters.

SUMMARY OF THE INVENTION

It is in general an object of the invention to provide a new and improved catheter and tip marker and method of manufacturing the same.

Another object of the invention is to provide a catheter and method of the above character in which the tip marker is easy to install and does not interfere with other functions of the catheter.

These and other objects are achieved in accordance with the invention by providing a tip marker comprising a semi-cylindrical sleeve of radiopaque material having an arc length less than 360°. In one embodiment, the tip marker is crimped in position about an inner tubular member, and an outer tubular member is bonded to the inner tubular member, with the tip marker being captured between the two members. In this particular embodiment, the outer tubular member comprises an inflatable balloon, and a vent opening extends from the balloon to the distal end of the catheter through the gap formed between the confronting edges of the marker sleeve.

DETAILED DESCRIPTION OF THE INVENTION

Figure 1:
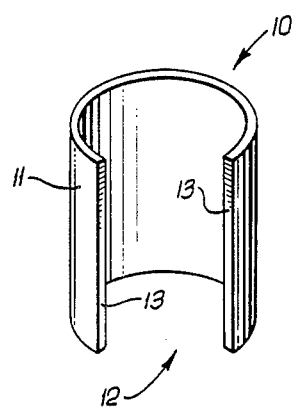
FIG. 1 is an isometric view of one embodiment of a tip marker according to the invention.

As illustrated in FIG. 1, the tip marker 10 comprises a generally semi-cylindrical sleeve 11 of radiopaque material having an arc length of less than 360°, with a gap 12 between the confronting edges 13 of the sleeve. In one presently preferred embodiment, the split, cylindrically shaped sleeve has an arc length of 270° and a gap of 90°. However, the sleeve can have any desired arc length between 180° and 360°.

In one presently preferred embodiment for use in a balloon dilatation catheter, the sleeve is fabricated of gold, and it has a length on the order of 0.040-0.045 inch, a wall thickness on the order of 0.003 inch and an internal diameter corresponding to the diameter of the catheter or other device on which the marker is to be mounted. The semi-cylindrical sleeve is conveniently fabricated from a cylindrical sleeve by cutting away a portion of the side wall of the sleeve.

Figure 2:
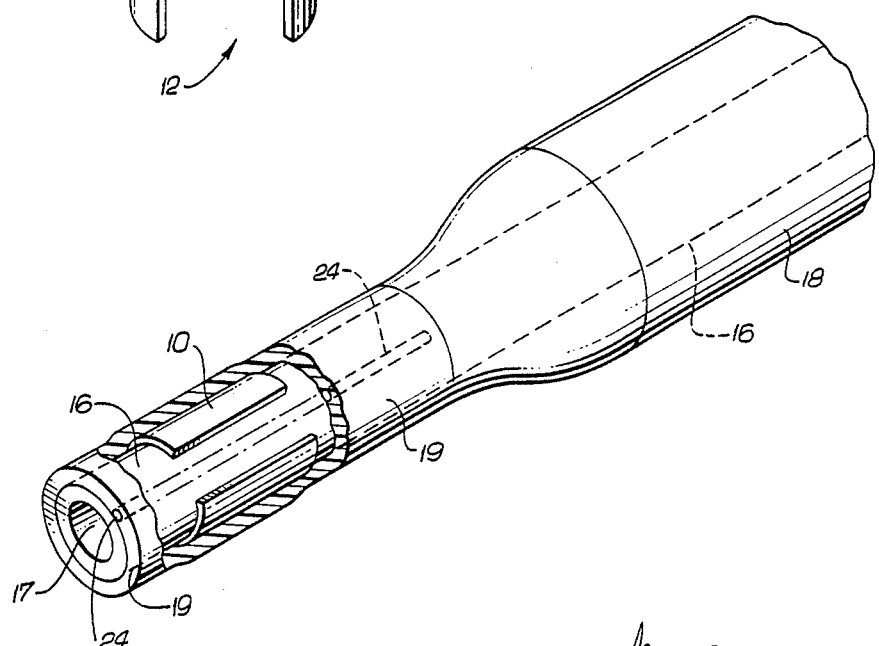
FIG. 2 is a fragmentary isometric view, partly broken away, of one embodiment of a dilatation catheter with a tip marker according to the invention.
Figure 3:
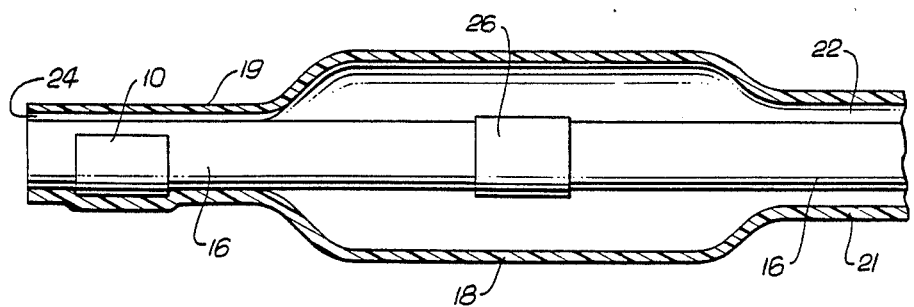
FIG. 3 is a fragmentary centerline sectional view of the embodiment of FIG. 2.

The catheter illustrated in FIGS. 2-3 includes an inner tubular member or shaft 16 having an axially extending lumen 17 adapted to receive a guide wire. An inflatable balloon 18 is mounted on the shaft near the distal end of the shaft. In the embodiment illustrated, the balloon comprises a tubular member which extends the full length of the catheter with a distensible portion forming the balloon itself. The distal end portion 19 of the outer tubular member is bonded to the distal end portion of the inner tubular member to seal the distal end of the balloon chamber. The proximal end portion of the outer tubular member is spaced coaxially from the inner tubular member to form an annular passageway 22 for inflating and deflating the balloon.

A small vent opening 24 extends longitudinally between the distal end portion of the balloon and the distal end of the catheter to permit trapped gases to be evacuated from the balloon. This opening is of a size large enough to pass the gas molecules but small enough to prevent the passage of liquid. This opening typically has a diameter on the order of 0.0006 inch, and in the embodiment illustrated, it is formed at the junction of tubular members 16, 19.

A tip marker 10 of the type illustrated in FIG. 1, is provided near the distal end of the catheter. The marker is located between tubular members 16, 19, with vent opening 24 extending through the gap between the confronting edges of the marker sleeve.

A second marker 26 is mounted on inner tubular member 16 toward the midpoint of balloon 18. This marker comprises a band of radiopaque material such as gold. In a preferred method of manufacture, the split tip marker sleeve 11 is positioned near the distal end of inner tubular member 16 and crimped about that member to hold it in position temporarily. Marker 26 is positioned on the inner tubular member and affixed by suitable means such as cementing. A longitudinally extending mandrel such as a tungsten wire (not shown) is temporarily affixed to the outer surface of tubular member between the confronting edges of sleeve 11 to form vent opening 24. The outer tubular member 19 is then positioned over the inner tubular member, and the distal end portions of the tubular members are bonded together by heat sealing to close the distal end of the balloon and to capture the tip marker sleeve between the members. The tungsten wire mandrel is then removed to form the vent opening.

Operation and use of the catheter are as follows. The catheter is positioned in the vascular system of a patient over a guide wire (not shown) which passes through lumen 17. The position of the tip of the catheter and the balloon can be observed fluoroscopically by means of markers 10, 26. Pressurized fluid is introduced into balloon 18 through annular passageway 22 to inflate the balloon, with any gas trapped in the balloon being expelled through vent opening 24.

The invention has a number of important features and advantages. The split marker sleeve can be used where conventional markers cannot be used. It does not interfere with other functions such as the vent opening for the balloon. Moreover, it can be crimped to hold it in position temporarily while a catheter is being assembled.

It is apparent from the foregoing that a new and improved catheter, tip marker and method of manufacturing the same have been provided. While only certain presently preferred embodiments have been described in detail, as will be apparent to those familiar with the art, certain changes and modifications can be made without departing from the scope of the invention as defined by the following claims.

I claim:

1. A vascular catheter comprising:
   (a) an elongated flexible outer tubular member having proximal and distal ends and an inflatable balloon near the distal end thereof defining an interior chamber therein;
   (b) a vent passageway extending distally from the balloon interior providing fluid communication with the surrounding exterior environment; and
   (c) a split, cylindrically shaped sleeve of radiopaque material disposed distally of the inflatable balloon having an arc length of less than 360° and a longitudinal gap between the confronting edges thereof with the vent passageway disposed within the gap.

2. The catheter of claim 1 wherein the sleeve has an arc length on the order of 270° C.

3. The catheter of claim 1 wherein the sleeve is fabricated of gold.

4. The catheter of claim 1 including a flexible elongated inner tubular member disposed within the first mentioned tubular member with the distal end of both tubular members secured together with the split cylindrically shaped sleeve disposed therebetween.

5. In a method of manufacturing a dilatation catheter having an inner tubular member, an outer tubular member having an inflatable balloon near the distal end, a vent passageway extending distally from the balloon providing fluid communication between the interior chamber thereof and the surrounding exterior environment, and a generally split, cylindrically shaped sleeve of radiopaque material with an arc length greater than 180° and less than 360° having a longitudinal gap between the confronting edges thereof to accommodate the vent passageway, the steps of: positioning the sleeve on the inner member, crimping the sleeve about the inner member to hold it in position, placing the outer member over the inner member and the sleeve, and bonding the outer member and the inner member together, with the sleeve being captured between the two members with the vent passageway disposed between the confronting edges of the marker.

6. The method of claim 5 wherein the two members are bonded together by heat sealing.

7. The method of claim 5 including the steps of positioning a longitudinally extending mandrel on the inner member in the gap between the confronting edges of the sleeve, and withdrawing the mandrel after the two members are bonded together to form a longitudinally extending passageway between the members.

* * * * *